United States Patent [19]
Hon et al.

[11] Patent Number: 5,215,090
[45] Date of Patent: Jun. 1, 1993

[54] FETAL ELECTRODE

[76] Inventors: Edward H. Hon, 11 Bradbury Hills Rd., Bradbury, Calif. 91010; Hon Edward D., 1325 6th Ave., San Francisco, Calif. 94122; Robert W. Hon, 483 Panchita Way, Los Altos, Calif. 94022

[21] Appl. No.: 668,158

[22] Filed: Mar. 12, 1991

[51] Int. Cl.⁵ .......................... A61B 5/0448
[52] U.S. Cl. ....................... 128/642
[58] Field of Search ............... 128/642, 775, 778, 788

[56] References Cited

U.S. PATENT DOCUMENTS

| | | | |
|---|---|---|---|
| 3,827,428 | 8/1974 | Hon et al. | 128/642 |
| 4,301,806 | 11/1981 | Helfer | 128/642 |
| 4,321,931 | 3/1982 | Hon | 128/642 |
| 4,577,635 | 3/1986 | Meredith | 128/642 |
| 4,813,425 | 3/1989 | Malis | 128/642 |
| 4,836,208 | 6/1989 | Ulbrich | 128/642 |
| 4,913,151 | 4/1990 | Harui et al. | 128/642 X |

FOREIGN PATENT DOCUMENTS 205335 12/1983 Fed. Rep. of Germany ...... 128/642
786985 12/1980 U.S.S.R. ...................... 128/642

*Primary Examiner*—Lee S. Cohen
*Attorney, Agent, or Firm*—Lewis Anten

[57] ABSTRACT

A fetal monitoring scalp electrode apparatus has a relatively rigid form sustaining curved outer guide tube and a flexible inner driver tube movable within the outer guide tube for driving an electrode holder holding an electrode which is screwed into the head of a fetus in the womb. The outer guide tube has a substantial angularity or bend proximate the forward end. Finger engaging projections, or other irregularity, are provided on the exterior of the outer guide tube, proximate the substantial angularity, for positioning of the apparatus and assuring that the force vector created during use of the device is toward the fetus. Pushing of the inner driver tube causes rotation of the holder and the electrode mounted in it. In an alternative embodiment, the inner driver tube has a highly flexible portion, such as a coil spring, proximate the substantial angularity or bend of the outer guide tube, permitting smooth rotation of the internal driver tube and electrode.

24 Claims, 4 Drawing Sheets

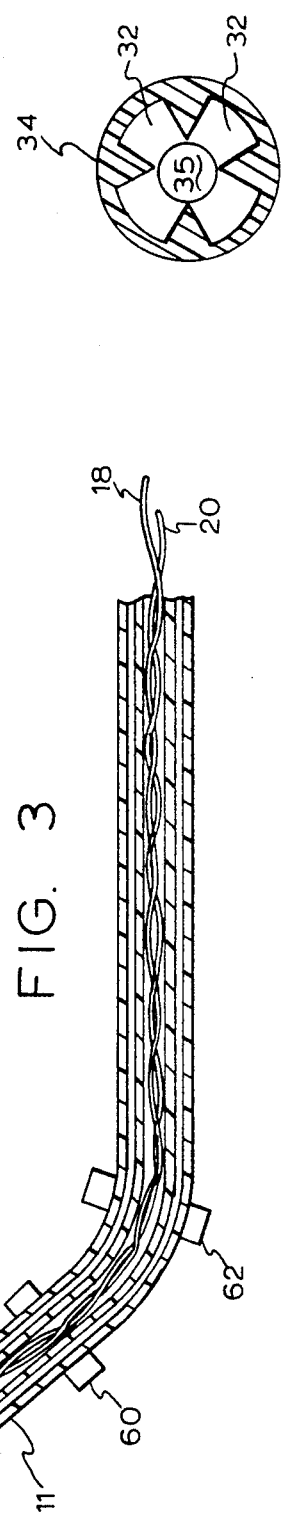
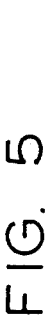
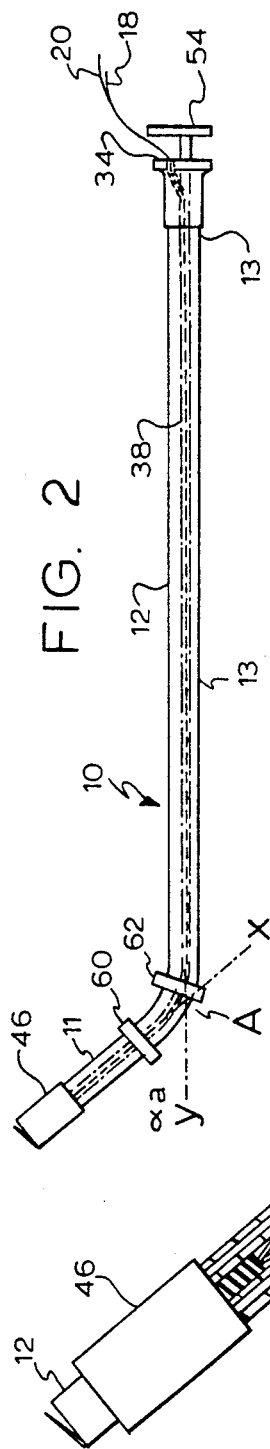
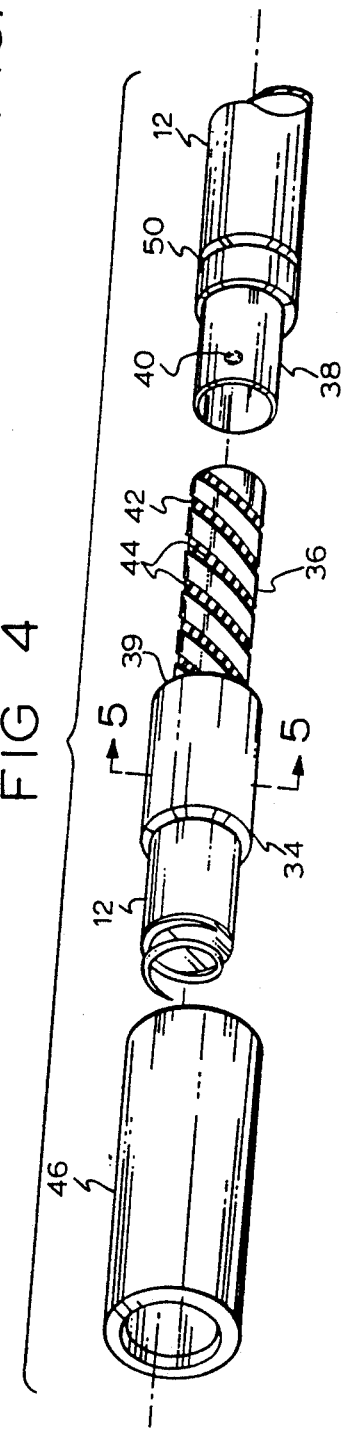

FETAL ELECTRODE

BACKGROUND

The present invention relates to a device for inserting a bipolar electrode structure through the vagina and cervix of a woman in labor and attaching it to the epidermis of a fetus. The electrode structure is designed to be operatively connected to an amplifier and a cardiotachometer for recording the fetal electrocardiogram and heart rate during labor and delivery.

For over seventy years monitoring of the fetal heart rate has been one of the important procedures in the management of labor. A number of electronic techniques have been developed for continuous recording of this data. Currently, the most successful techniques for fetal heart rate monitoring employ electrode attached directly to the scalp of the fetus.

U.S. Pat. No. Re. 28,990 issued to Dr. Edward H. Hon, is directed to an electrode structure which is believed to be the most widely used type employed today in the monitoring of fetal heart rate. The state of the art prior to the development of the device disclosed in that patent is amply illustrated in the references cited during the prosecution of the application for that patent.

The device of U.S. Pat. No. Re. 28,990 has a number of disadvantages. Firstly, the angularity of the outer guide tube must be kept relatively small, about 22 degrees, with respect to its primary longitudinal axis in order to permit the inner driver tube to rotate smoothly within the outer guide tube. The radius of curvature is about 12-13 inches. If the angle is too great the inner driver tube would cause friction at the bend and result in a jerky release of the inner drive tube preventing smooth continuous rotation of the electrode. All feel would be lost This small angle also mandates that the arms of the doctor be kept very low in relationship to the axis of the vagina of the patient, at the plane of the top of the bed the patient is lying on, in order to permit the device to be applied to the head of the fetus. This is especially true if the head of the fetus is high, as it often is in early labor. This situation may be present during the last few weeks of pregnancy or at the commencement of labor. In many multiparous and some nulliparous women, at the onset of labor the fetal head is above the pelvic inlet. In this circumstance, the head is referred to as high or "floating." Additionally, the cervical canal may be minimally (1-2 in) dilated an its axis makes an angle of 90-100 degrees with the axis of the vagina. This combination of factors viz., high head, minimal cervical dilation and axial misalignment makes electrode application extremely difficult with an electrode system when the guide tube curvature is too "flat" to negotiate the acute angles encountered in the foregoing circumstance.

A second disadvantage of this prior device is that the electrode is rotated by the physical rotation of the hand in order to implant the electrode in the head of the fetus. This is not a simple procedure and is inherently awkward as a complete turn of the driver tube is required and usually requires two separate turns of about 180 degrees each. In the interval between turns when the driver is released, it may "kick back" (due to friction at the curvatures), thus further complicating application. The turning action, coupled with the smooth guide tube, tends to create a rearward, away from the fetus, vector force during use. This may result in the electrode sometimes being withdrawn from the head of the fetus during rotation, preventing the implanting of the electrode in the head of the fetus.

Patents have disclosed guide tubes which can vary the angle of the guide tube, such as disclosed in U.S. Pat. No. 4,686,996 and U.S. Pat. No. 4,836,208 to Ulbrich. In the Ulbrich patent a flexible guide tube has a portion which is a flexible universal hinged member. The electrode holder is affixed to the end of the guide tube, and the entire guide tube is rotated. These patents evidence the inability of prior devices to increase the angle of the outer guide tube and still have an internal driver. With such devices, it would be difficult to apply the electrode due to the flexibility of the joint, and it could even move out of the line of the guide tube.

In the United States Patent to Murphy, U.S. Pat. No. 4,149,528 a highly flexible outside guide tube was used with flexible wires, without an inner drive tube. The increased angle of the outer guide tube required the elimination of the inner guide tube.

These patents resulted in devices that would be more difficult to use, more expensive than the currently acceptable and familiar device, and also less reliable.

The electrode of U.S. Pat. No. 4,321,931, issued to Edward D. Hon, avoids rotation of the hand. This patent provided a plunger rod arrangement for converting a linear pushing action into a rotary action at the electrode tip end for advancing and rotating the electrode at the same time. However, such a device may generate an even greater rearward vector force than the prior device since the physician reflexly pulls back on as any device that has a syringe-like action. Also, the angularity of the device was substantially the same as the original electrode of U.S. Pat. No. Re. 28,990.

Also, the outer guide tubes of the prior art electrode devices are smooth and are made slippery by the natural lubricating secretions present in the vagina. During application of the electrode there was no means of firmly holding the forward end of the guide tube to maintain gentle pressure against the fetus during application, or for determining the axial direction of the outer guide tube with respect to the axis of the head of the fetus.

SUMMARY OF THE INVENTION

The present invention comprises a spiral fetal electrode in which a relatively rigid form sustaining outer guide tube has a substantial angularity of greater than 30 degrees, preferably in the order of about 45 degrees, proximate the forward end of the guide tube. Such angularity existing between the primary axis of the proximal end (about ⅔) of the guide tube and its distal ⅓. This greater angularity approximates the axial relationship of the cervix and vagina, especially in early labor, so that the physicians' arms and elbows do not have to be low at the level of the patients' bed during application.

The present invention also includes finger engaging members attached to the outside of the outer guide tube proximate the angularity of the outer guide tube for assisting in grasping the guide tube in order to hold it against the head of the fetus during application of the electrode holder, and also for controlling the orientation of the guide tube in relationship to the head of the fetus. Further, the finger engaging member assists in directing the vector forces created toward the head of the fetus. The finger engaging members are preferably in the form of two or more doughnut like members, having flattened opposite sides, surrounding the outer guide tube. However, other forms of finger engaging means, such as projections or depressions in the outer guide tube may be used. The flattened sides of the finger engaging member permit the physician to more easily determine the orientation of the guide tube.

In the preferred embodiment, a hollow tubular driver tube which has two dimples in its distal end and is pushed against a spirally-grooved electrode holder at the front of the guide tube. The driving and rotation elements of the system are so designed that electrode rotation is limited to one turn, hence eliminating the possibility of over rotation which can be done with all other fetal electrodes. Moreover, when one turn has been achieved this is indicated to the fingers holding the engaging member by a gentle rearward force. Pushing the inner driver tube against the rear of the electrode holder causes the electrode holder and electrode tip to first advance and then to rotate, screwing the electrode into the head of the fetus.

In an alternative embodiment, the inner driver tube has a separate highly flexible portion, preferably a coil spring, proximate the angularity of the outer guide tube permitting the inner driver tube to rotate smoothly within the outer guide tube to rotate the electrode. The highly flexible spring of the driver tube permits the physician to receive "feed back" or "feel" so the physician knows whether the electrode tip has engaged the head of the fetus or is merely turning in the air.

OBJECTS OF THE INVENTION

It is an object of the present invention to provide a fetal electrode applicator that is easier to use.

It is another object of the present invention to provide a fetal electrode applicator that is safer to use.

It is yet another object of the present invention to provide a fetal electrode applicator that is more reliable;

It is still another object of the present invention to provide a fetal electrode applicator that is simple to make;

It is another object of the present invention to provide a electrode assembly that uses screws into the fetal epidermis as present electrodes.

These and other objects of the present invention will be more apparent after a review of the following specification and accompanying drawings.

BRIEF DESCRIPTION OF DRAWINGS

FIG. 2 is a side partial sectional view of the fetal electrode assembly of the present invention.

FIG. 3 is a side sectional view of the lower portion of distal the fetal electrode.

FIG. 4 is a perspective exploded view of the tip of the electrode.

FIG. 5 is a sectional view taken along line 5—5 of FIG. 4.

DETAILED DESCRIPTION OF THE DRAWINGS

Figure 1:
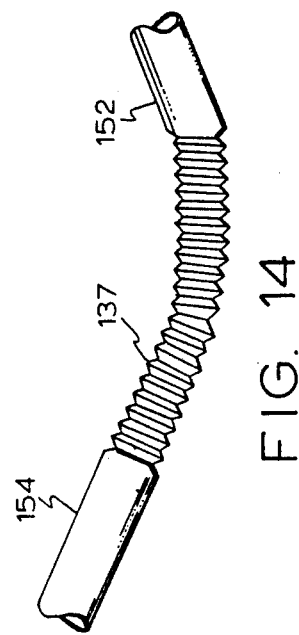
FIG. 1 is a side view of the first preferred embodiment of the present invention being applied to the fetus.

Referring to FIGS. 1 through 9, the preferred embodiment of the present invention is shown. An electrode assembly structure 10 comprises a hollow outer guide tube 12 having an electrode holding member 16 in the forward end 11 connected to electrode wires 18 and 20 which extend from the rear end 13. The outer guide tube 12 is curved and relatively rigid so as to be form-sustaining to facilitate insertion of the tube through the vagina and cervix of a woman in labor as shown in FIG. 1.

Figure 2A:
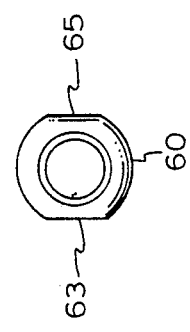
FIG. 2A is a front view of the projecting gripping members.

As shown in FIG. 2, the outer guide tube 12 has a substantial angularity, or bend, A towards its forward end 11. The angle "a" is formed by the central longitudinal axis X of the forward portion 11 of the outer guide tube 12 with the central longitudinal axis Y of the rear portion 13 of the guide tube. The angle "a" is preferably 35-55 degrees, although the angle may be as little as 30 degrees or greater than 55 degrees if desired. Considering the angularity A as generally an arc of a circle, the radius of curvature of the arc would be approximately 4½ inches.

Figure 13:
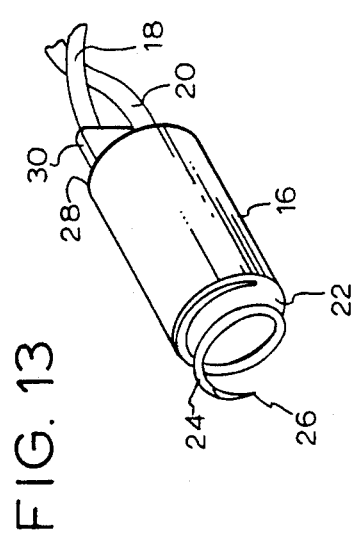
FIG. 13 is an enlarged view of the electrode holder and driver tube attachment.

Referring to FIG. 13, the front face 22 of the electrode holder 16 has an electrode retaining coil 24 mounted thereon and is provided with a pointed forward end 26 to pierce the fetal epidermis. The front face 22 of the electrode holder 16 acts as a stop which limits the distance which the coil 24 can travel into the fetus. The distance between the point 26 of the retaining coil 24 and the front face 22 of the electrode holder 16 is relatively small (e.g. about 1/16 of an inch). The rear face 28 of the electrode holder 16 has projecting engaging fins 30 for engaging corresponding slots 32 in the inside of surrounding rotation transition member 34 having an opening 35 there through.

The fins 30 are adapted to be releasably engaged by the slots 32. The connection between the fins 30 and the slots 32 is relatively "loose" so the fins will "slip" when the electrode holder 16 meets with a relatively slight amount of resistance to rotation. Thus, when the electrode holder 16 meets with resistance to rotation (e.g. when the retaining coil 24 has pierced the fetal epidermis and the front face 22 of the electrode holder 16 has come into contact with the fetus), continued rotation of the rotation of the rotation transmission member 34 will not drive the retaining coil 24 further into the fetus. This "loose driving connection" may be accomplished by making the fins 30 of the driver tube between the slots 32 "soft" or pliable enough so that they will bend and "slip" relative to one another when the holder 16 resists rotation. Other variations of slipping devices may similarly be used, such as friction fits, irregular diameters and the like. A spirally grooved tubular extension 36 extends from the base 39 of the rotation transition member 34. The spiral grooves 36 fits within hollow inner driver means 38 in the form of a tube. While in the preferred embodiment, a tube is used, a push rod or other means may be used as well. Projections 40 and 41 extend from the inside wall of the hollow inner driver tube 38 for engaging the spiral grooves 42 of spiral tubular extension 36. The spiral grooves 42 have serrations or irregularities 44 on the bottom of the spiral, acting as a ratchet means as the projections 41 and 42 engage the serrations 44. This provides the physician with additional feel as the electrode holder 16 is advanced. The projections 40 and 41 frictionally engage the spiral tubular extension 36.

A hollow tubular cap 46 fits over the electrode holder 16 and snap fits over he end of the outer guide tube 12 by means of a circumferential projection 48 on the interior of the cap, a circumferential slot 50 in the outer wall of the outer guide tube 12. The end of the cap has a covering 53 with an opening 52 sufficient to permit the electrode holder 16 to pass through the opening 52, but not the rotation transition member 34.

The outer guide tube 12 is more rigid than the flexible driver tube 38 so that the outer guide tube 12 will maintain its curved configuration when the flexible inner driver tube 38 is advanced longitudinally within it. The flexible inner driver tube 38 is hollow and preferably made of plastic and extends within the outer guide tube 12 for frictional engagement with the spiral tubular extension 36. The rear end 54 of the inner driver tube 38 extends beyond the rear end of the outer guide tube 12, terminating in an enlarged end. The rear end 54 has a smooth opened portion to reduce the likelihood that the device will be held like a syringe. In the preferred embodiment, the rear end of the inner driver tube 38 has means for preventing its rotation, such as a slot and pin arrangement.

As shown in FIG. 2, the wires 18 and 20 pass through the rotation transition member 34 and the hollow inner driver tube and out the rear of the driver tube 38. A smooth plunger element 54 is attached to the projecting end of the inner driver tube 38.

Finger engaging projections 60 and 62 surround the outer guide tube 12, proximate the angularity A, spaced about one inch apart. The finger engaging members 60 and 62 are in the form of annular rings, much like a doughnut. The finger engaging projections 60 and 62 are about 12 mm in diameter and have flat segments 63 and 65, or other indicating means, for indicating the orientation of the front end of the guide tube 12 relative to the head of the fetus. While in the preferred embodiment, two or more such finger engaging members 60 and 62 are used, a single finger engaging member may also be used. Further, the finger engaging members 60 and 62 may be formed integrally with the outer guide tube 12 and may be in the form of a raised portion, or depression of flattened portion for permitting the fingers to firmly hold of the outer guide tube 12.

Figure 6:
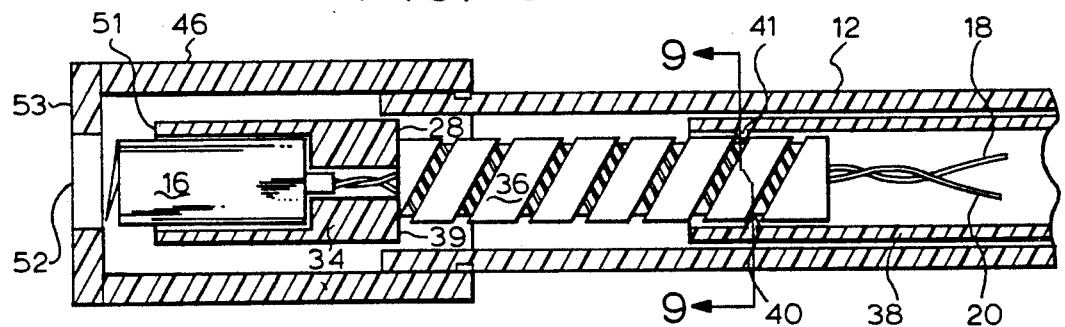
FIG. 6 is a side sectional view of the position of the tip prior to use.
Figure 7:
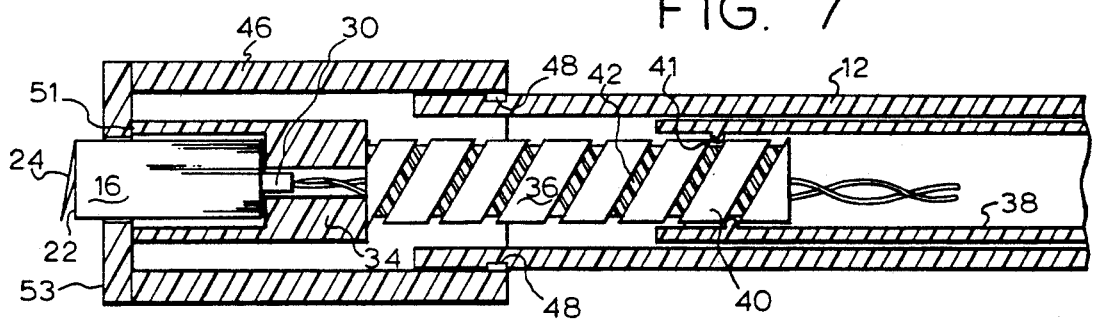
FIG. 7 is a side sectional view of the points of the tip longitudinal axial after initial its lateral movement prior to rotation.
Figure 8:
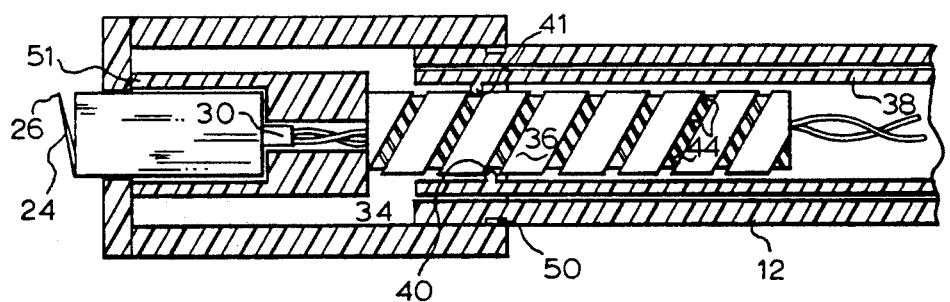
FIG. 8 is a side sectional view of the position of the tip during its rotational movement.
Figure 9:
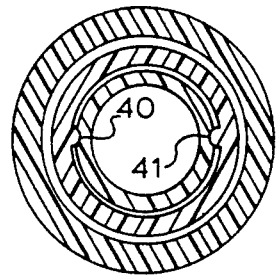
FIG. 9 is a sectional view along lines 9—9 of FIG. 6

Application of the electrode assembly 10 is accomplished as shown in FIGS. 6-8.

As shown in FIG. 6 the initial position of the electrode holder 16 is recessed from the opening 52 of the cap 46 as is the forward end 51.

As shown in FIG. 7, the inner driver tube 38 has its projections 40 and 41 frictionally engaging the spiral tubular extension 36. As the inner driver tube 38 is pushed, due to the frictional engagement of the projections 40 and 41 with the spiral grooves 42, advancement of the driver tube causes the rotational transition member 36 and the electrode holder 16 to advance forward, without any rotation. The entire electrode holder advances forward until the front edge 51 of the rotational transition member 34 hits the inside of the covering 53 preventing any further advancement of the rotation transition member 34. The electrode holder 16 projects through the opening 52 of the cap 46 as shown in FIG. 7.

Further forward movement of the inner driver tube 38 causes the projections 40 and 41 within the spiral 42 to cause the rotation of the transition rotation member 34, the electrode holder 16 and electrode, as shown in FIG. 8. Once the front face of the holder is reached, penetration will be prevented and the fins will slip into the slot. Advancing the electrode holding member 16 before causing it to rotate improves the attachment process by not having the electrode 24 start rotation until it is in contact with the fetus, and also reduces the total rotation required for the electrode 24, thereby reducing the path of travel of the spiral.

Other means of rotating the electrode holder 16 may be employed, such as by a gear driven mechanism or the push rod disclosed in Hon Patent No. 4,321,931.

Figure 11:
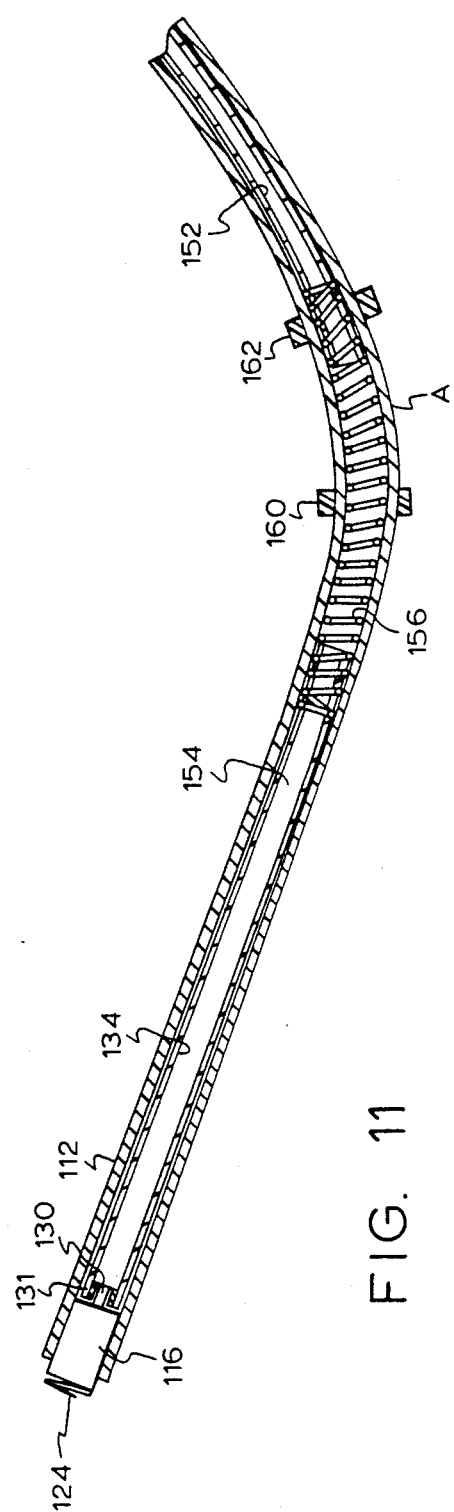
FIG. 11 is a side sectional view of the device of FIG. 10.
Figure 12:
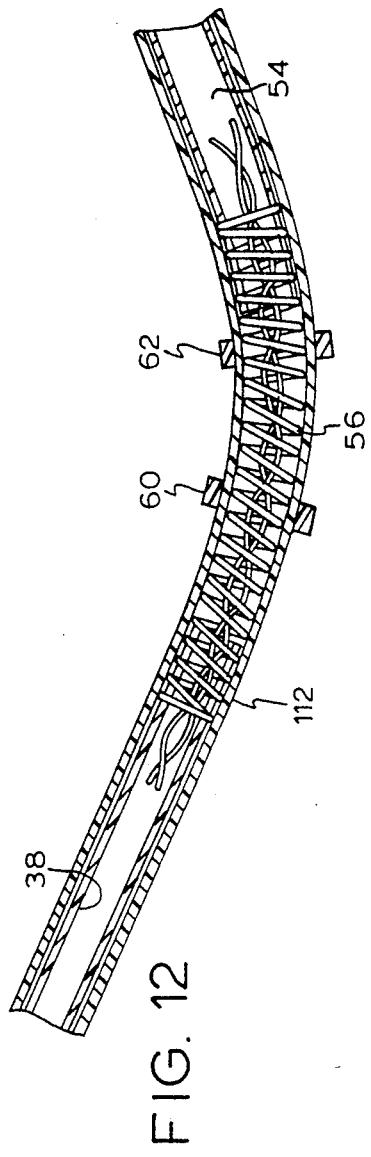
FIG. 12 is a side sectional view of the highly flexible spring portion showing the position of the wires of the electrode.
Figure 10:
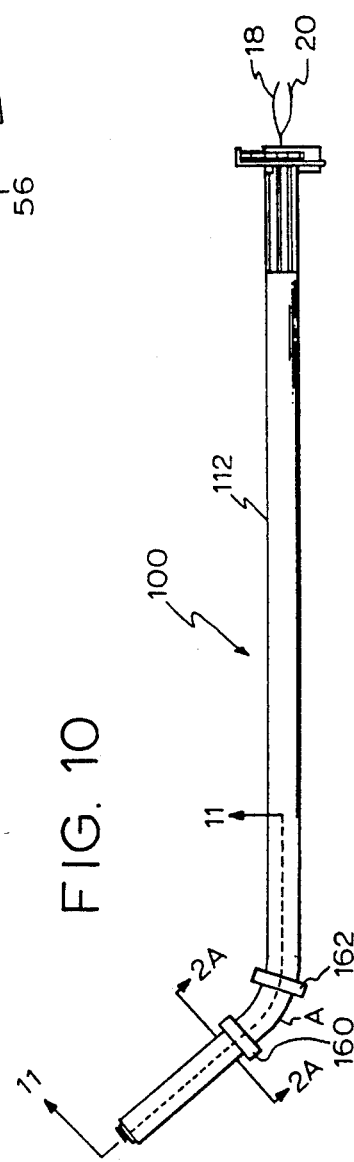
FIG. 10 is a side view showing an alternative embodiment having a universal joint member.

In an alternative embodiment shown in FIGS. 10-12. A relatively rigid outer guide tube 112 has an angularity A proximate the forward end of the assembly 100. Finger engaging projections 160 and 162 are positioned proximate the angularity A. Inner driver tube 134 comprises a hollow tubular member having a first upper portion 152 and a second lower portion 154, and a highly flexible central hinge segment 56, preferably in the form of a spiral spring, proximate the angularity A in the outer guide tube 112, between the first upper portion 152 and the second lower portion 154. It is preferable to have the coil spring 156 orientated so that it tightens when rotated to avoid the spring 156 expanding and engaging the inside walls of the outer guide tube 112. The spiral spring 156 serves as a universal joint or swivel permitting smooth full rotation of the flexible inner driver tube 138 within the outer guide tube 112.

Figure 14:
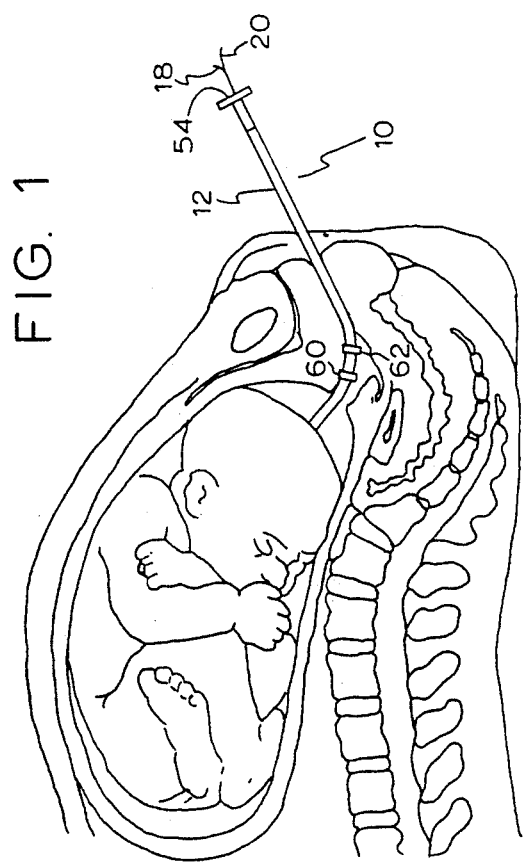
FIG. 14 is an alternative embodiment for the universal joint member.

Referring to FIG. 14, a universal ribbed hinged member 137, such as commonly used in a flexible drinking straw, is shown in place of the spring. Other highly flexible members may be used such as thin rubber tubing. The coil spring 156 permits essentially frictionless rotation within the outer guide tube and thereby provides the physician ca feel when the electrode is fully rotated into the fetal epidermis.

The electrode holder 116 and driver tube 134 is disposed within the outer guide tube 112, with the fins 130 engaging slots 131 in the forward end of the inner driver tube 134. The doctor inserts the forward end of the outer guide tube 112 through the vagina and cervix as shown in FIG. 1 until the plane of the opening of the forward end of the outer guide tube 112 is tangent to and in contact with the fetal head. While supporting the outer guide tube 112 by the fingers against the finger engaging projections 160 and 162. When the doctor feels that the retaining coil 24 has contacted the fetal epidermis, he rotates the flexible inner driver tube 134 while maintaining the forward end of the outer guide tube 112 against the fetal head. This will screw the retaining coil 124 into the epidermis. Due to the flexible coil spring coupling 156, the physician will "feel" the "rebound" of the rear end of the inner driver tube 134 when the retaining coil spring 124 is fully rotated into the epidermis covering the fetal head. Once the retaining coil spring 124 is in place the outer guide tube 112 is withdrawn and the electrode wires are connected to a monitor.

It is appreciated that other embodiments of the present invention may be devised which do not differ from the inventive concept herein disclosed.

What is claimed is:

1. Apparatus for use in monitoring fetal heartbeat and similar vital functions comprising;

a relatively rigid form sustaining curved outer guide tube having a forward end and a rear end adapted to have its said forward end inserted through the vagina and cervix of a woman in labor; and a flexible inner driver tube within said outer guide tube, said outer guide tube being more rigid that said inner driver tube;

an electrode holder member having an electrode retaining coil at one end, said electrode holder member rotatably disposed in said outer guide tube;

said retaining coil mounted on said electrode holder member and adapted to be screwed into a fetal epidermis by rotating said electrode holder member;

said electrode holder member capable of being rotated to screw said retaining coil into the fetal epidermis responsive to rotation of said inner driver tube within said outer guide tube, said outer guide tube having an angularity proximate said forward end of greater than 30 degrees.

2. The apparatus of claim 1 in which said angularity is about 45 degrees.

3. The apparatus of claim 1 in which said angularity has a radius of curvature of less than 10 inches.

4. The apparatus of claim 1 in which said angularity has a radius of curvature of about 4 inches.

5. The apparatus of claim 1 in which said inner driver tube rotates within said outer guide tube.

6. The apparatus of claim 1 in which said inner driver tube moves longitudinally within said outer guide tube.

7. The apparatus of claim 6 in which said inner driver tube comprises a hollow tube.

8. The apparatus of claim 6 in which said outer guide tube has finger engaging means proximate said forward end of said outer guide tube.

9. The apparatus of claim 1 in which said outer guide tube has finger engaging means proximate said forward end of said outer guide tube.

10. The apparatus of claim 1 in which the holder member includes a spiral, whereby longitudinal movement of said inner driver tube causes said spiral member to rotate, thereby causing rotation of said electrode holder member and said electrode retaining coil.

11. The apparatus of claim 10 in which said spiral member includes irregularities on a depressed surface portion of said spiral member.

12. Apparatus for use in monitoring fetal heartbeat and similar vital functions comprising;

a relatively rigid form sustaining curved outer guide tube having a forward end and a rear end and adapted to be inserted through the vagina and cervix of a woman in labor; a flexible inner driver tube movable within said curved outer guide tube;

an electrode holder member having an electrode retaining coil at one end, said electrode holder member disposed in said outer guide tube;

said retaining coil mounted on said electrode holder member and adapted to be screwed into a fetal epidermis by rotating said electrode holder member;

said electrode holder member capable of being rotated to screw said retaining coil into the epidermis; said outer guide tube being more rigid that said inner driver tube so that said outer guide driver tube will maintain its curved configuration when said flexible tube is moved within it, said outer guide tube having at least one finger engaging means associated with said outer guide tube proximate said forward end of said outer guide tube, said finger engaging means comprising a ring like projecting member.

13. The apparatus of claim 12 in which at least one said ring like projecting member includes at least one flattened portion.

14. The apparatus of claim 12 in which said outer guide tube has a bend proximate said forward end, said bend being greater than 30 degrees.

15. The apparatus of claim 14 in which said bend is between 40 and 50 degrees.

16. Apparatus for use in monitoring fetal heartbeat and similar vital functions comprising:

a relatively rigid form sustaining curved outer guide tube having a forward end and a rear end adapted to have its said forward end inserted through the vagina and cervix of a woman in labor and a flexible inner driver tube within said outer guide tube, said outer guide tube being more rigid that said inner driver tube;

an electrode holder member having an electrode retaining coil at one end, said electrode holder member rotatably disposed in said outer guide tube;

said retaining coil mounted on said electrode holder member and adapted to be screwed into a fetal epidermis by rotating said electrode holder member; said electrode holder member capable of being rotated to screw said retaining coil into the fetal epidermis responsive to rotation of said inner driver tube within said outer guide tube, said outer guide tube having an angularity proximate said forward end of greater than 30 degrees whereby advancement of said inner driver tube advances said electrode holder member longitudinally so that said electrode retaining coil extends beyond the forward end of said outer guide tube before rotating said electrode holder member.

17. Apparatus for use in monitoring fetal heartbeat and similar vital functions comprising:

a relatively rigid form sustaining curved outer guide tube having a forward end, a rear end, and inside walls, having its forward end adapted to be inserted through the vagina and cervix of a woman in labor;

an electrode holder member having a coil electrode at one end, said electrode holder member slidably and rotatably disposed in the forward end of said outer guide tube;

said coil electrode mounted on said electrode holder member and adapted to be screwed into a fetal epidermis by rotating the electrode holder member;

a flexible inner driver tube slidably and rotatably disposed within said curved outer guide tube for rotating said electrode holder member to screw said coil electrode into the epidermis; said outer guide tube being more rigid that said driver tube so that said outer guide tube will maintain its curved configuration when said flexible driver tube is rotated within it;

said inner driver tube having a universal joint between its ends whereby said inner driver tube may be freely rotated within said outer guide tube without interference from the inside walls of said outer guide tube.

18. The apparatus of claim 17 in which said universal joint comprises a spring member.

19. The apparatus of claim 18 in which said spring member comprises a coil spring.

20. The apparatus of claim 17 in which said outer guide tube has a bend of between 30 and 55 degrees proximate said forward end.

21. The apparatus of claim 17 in which said outer guide tube has an angularity of greater than 30 degrees proximate said forward end.

22. The apparatus of claim 21 including finger engaging means proximate said forward end of said outer guide tube.

23. The apparatus of claim 17 including finger engaging means proximate said forward end of said outer guide tube.

24. The apparatus of claim 17 in which said universal joint comprises a universal ribbed hinged member.

* * * * *